United States Patent [19]

Roscher et al.

[11] Patent Number: 4,894,470

[45] Date of Patent: Jan. 16, 1990

[54] PROCESS FOR THE PREPARATION OF DIALKYL VINYLPHOSPHONATES

[75] Inventors: Günter Roscher, Kelkheim; Hans-Jerg Kleiner, Kronberg/Taunus; Gabriele Ihl, Frankfurt am Main; Hermann Leipe, Kelkheim, all of Fed. Rep. of Germany

[73] Assignee: Hoechst Aktiengesellschaft, Frankfurt am Main, Fed. Rep. of Germany

[21] Appl. No.: 163,797

[22] Filed: Mar. 3, 1988

[30] Foreign Application Priority Data

Mar. 6, 1987 [DE] Fed. Rep. of Germany ....... 3707149

[51] Int. Cl.$^4$ ............................................... C07F 9/40
[52] U.S. Cl. .................................................... 558/142
[58] Field of Search ......................................... 558/142

[56] References Cited

U.S. PATENT DOCUMENTS 4,386,036 5/1983 Kleiner et al. ...................... 558/142

Primary Examiner—Anton H. Sutto

[57] ABSTRACT

A process for the production of dialkyl esters of vinyl phosphonic acid which comprises subjecting dialkyl esters of 2-acetoxyethane phosphonic acid to cleavage by contacting with a liquid catalytically acting medium at a temperature in the range from 150° to 270° C. and under a pressure such that the partial pressures of the total of the components of the reaction system is in the range from 1 to 500 mbar, and drawing off the resulting dialkyl esters of vinyl phosphonic acid and other volatile reaction products.

20 Claims, No Drawings

PROCESS FOR THE PREPARATION OF DIALKYL VINYLPHOSPHONATES

DESCRIPTION

Dialkyl vinylphosphonates are of importance as precursors for the preparation of pure vinylphosphonic acid and also as monomers for copolymerization for the preparation of adhesives or flameproof plastics. It has hitherto been possible to prepare them by various routes, but only in multi-stage procedures. Thus mixtures of vinylphosphonic acid derivatives which, in addition to monoalkyl vinylphosphonates and several other products, also contain small quantities (23% in the highest case) of dialkyl vinylphosphonates are obtained by the process of German Offenlegungsschrift 3,001,894 by heating dialkyl 2-acetoxyethanephosphonates at 150° to 270° C. in the presence of acid or basic catalysts.

In view of these unsatisfactory results, this process has been superseded by an improved two-stage process according to German Offenlegungsschrift No. 3,120,437, in which the alkyl acetate eliminated in the abovementioned reaction is distilled off, and the reaction product obtained as a bottom product is then reacted with orthoesters of carboxylic acids to give the desired dialkyl vinylphosphonates.

Thus none of the literature references mentioned describes the direct isolation of dialkyl vinylphosphonates which can be obtained as a distillate from the cleavage reaction and can subsequently be purified further by distillation.

It has now been found, surprisingly, that the cleavage of dialkyl acetoxyethanephosphonates does not take place in the manner described to give mixtures of derivatives of vinylphosphonic acid, but gives dialkyl vinylphosphonates directly, if dialkyl 2-acetoxyethanephosphonates are cleaved at 150° to 270° C., preferably at 180° to 250° C., at a partial pressure of the sum of the components in the reaction system between 1 and 500 mbar, preferably between 5 and 100 mbar, and in contact with a liquid medium having a catalytic action, and if the dialkyl vinylphosphonates and other volatile reaction products formed are removed in the form of vapor.

The expression "partial pressure of the sum of the components in the reaction system" embraces both the pressure of the dialkyl 2-acetoxyethanephosphonate and that of the reaction products formed therefrom, which are for the most part more volatile than the starting material and in this respect can be removed from the mixture by distillation. The pressure mentioned, for example between 10 and 100 mbar, can be obtained in various ways. In one embodiment the reaction is carried out under reduced pressure; in another procedure the reacton is carried out under a pressure of more than 500 mbar, it being possible to produce the difference between the total pressure and the desired partial pressure of the components in the reaction system by means of a gas which is inert towards the latter under the conditions of the reaction. Suitable inert gases of this type are those which are customary in practice, above all nitrogen, but also, if appropriate, carbon dioxide or light hydrocarbons, such as methane or ethane, and, in special cases, also noble gases, such as argon. It is, of course, also possible to use mixtures of various gases of this type.

Suitable media having a catalytic action are the same as those mentioned in German Offenlegungsschrift No. 3,120,437, specifically either acid or basic media. Examples of suitable acid media are sulfuric acid, phosphoric acid, halogen-containing carboxylic acids, such as dichloroacetic and trichloroacetic acids and also trifluoroacetic acid, aromatic sulfonic acids, such as benzenesulfonic and p-toluenesulfonic acids and vinylphosphonic acid, but, above all, products which are obtained from the byproducts produced as a bottom product in the present reaction, i.e. higher-boiling byproducts, by heating the latter with water, it being possible to carry out the treatment with water by, for example, boiling for a period of 5 minutes to 2 hours. Examples of basic media which can be used are tertiary aliphatic and aromatic amines ad phosphanes (previously described as phosphines), such as are also mentioned in large numbers in German Offenlegungsschrift No. 3,120,437.

The medium having a catalytic action is generally used in an amount of at least 0.1% by weight, relative to the dialkyl acetoxyethanephosphonate put through. The concentration in the reaction mixture is, naturally, substantially higher, since it acts as the reaction medium. In general, its amount is 1-20% by weight, it being, of course, preferable to use the smallest possible amounts, advantageously not more than 5% by weight, relative to the dialkyl acetoxyethanephosphonate put through. On the other hand, and this applies above all when using the byproducts of the reaction according to the invention which have been treated with water, it is also possible to use the media having a catalytic action in amounts even larger than 20% by weight without endangering the feasability of the reaction. The term % by weight relates in every case to the weight of dialkyl acetoxyethanephosphonate.

Although the present process is industrially suitable particularly for the preparation of dimethyl vinylphosphonate and diethyl vinylphosphonate, it is also possible to prepare esters having alkyl groups with more than two carbon atoms, such as propyl, isopropyl and the various butyl, pentyl, hexyl, heptyl and octyl groups. In general, therefore, the esters prepared in accordance with the invention contain alkyl groups having not more than 8, preferably not more than 4, carbon atoms, it being also possible to employ, and also to prepare mixed esters having different alkyl groups.

The process according to the invention can be carried out discontinuously, but also, with particular advantage, continuously, the cleavage products formed, especially the dialkyl vinylphosphonate, being removed continuously from the reaction mixture by distillation.

It was surprising that, under the conditions used in accordance with the invention, the dialkyl vinylphosphonates are obtained in a single process stage and in a high yield, although in the processes of the state of the art the only reaction to take place, under a higher pressure and otherwise similar conditions, is the elimination of alkyl acetates with the formation of monoalkyl vinylphosphonates and other compounds as residue products. A further advantage of the invention is that it is now possible to dispense with the use of the expensive ortho-esters of carboxylic acids for the preparation of pure dialkyl vinylphosphonates.

The dialkyl vinylphosphonates prepared in accordance with the invention can, if desired, also be purified further by distillation and, instead of, or after, this can also be hydrolyzed to vinylphosphonic acid or polymerized without further treatment.

The invention is illustrated by means of the following examples.

EXAMPLES (1) 50 g of crude vinylphosphonic acid were initially placed in a 1 litre stirred flask equipped with an offtake device for the sump and a distillation column mounted on the flask (internal diameter 25 mm, length 0.7 m, packed with 6 mm Raschig rings) having an automatic reflux divider, a distillation receiver, a cold trap placed downstream (low-temperature cooling by means of solid carbon dioxide) and an attached vacuum pump. The flask was heated to 210° C. and 200 g per hour of dimethyl acetoxyethanephosphonate were then introduced dropwise at 210° C. and under a pressure of 10 mbar. The reflux ratio in the column was set to 0.5.

The distillate obtained in the course of 5 hours was 650 g of a mixture containing 6.0% by weight of unreacted dimethyl acetoxyethanephosphonate, 80% by weight of dimethyl vinylphosphonate, 1.2% by weight of methyl acetate and 10% by weight of acetic acid. 226 g of a mixture containing 78% by weight of methyl acetate, 4% by weight of acetic acid and 7% by weight of dimethyl vinylphosphonate were obtained in the cold trap. The residue was 145 g of a mixture of various vinylphosphonic acid derivatives which, after heat treatment with water, are once more suitable as a catalyst for the present reaction.

The yield of dimethyl vinylphosphonate, relative to dimethyl acetoxyethanephosphonate reacted, was 80%.

(2) The experimental set-up was as in Example 1. After 50 g of vinylphosphonic acid had been put in and heated up to 210° C., a mixture of 95% by weight of dimethyl acetoxyethanephosphonate and 5% by weight of vinylphosphonic acid was metered in at a rate of approx. 140 g/h under a pressure of 10 mbar. When constant conditions have been set up, the level of the bottom product in the reaction flask was kept constant at a volume level of approx. 200 ml by continuously discharging sump material into a similarly evacuated vessel. The reflux ratio in the column was set to 1.

5,500 g were introduced in the course of 40 hours. This gave 3,200 g of distillate, 1,020 g of product from the cold trap and 1,225 g of material discharged from the sump.

After the sump material has been boiled up with water and the water removed by distillation, the material can be re-employed as a catalyst for cleaving the feed mixture. The distillate contained 89% by weight of dimethyl vinylphosphonate and 1.1% by weight of methyl acetate. The remainder was essentially acetic acid.

The product present in the cold trap contained 6% by weight of dimethyl vinylphosphonate, approx. 4% by weight of methanol and 3% by weight of acetic acid; the remainder was essentially methyl acetate.

The yield of dimethyl vinylphosphonate, relative to dimethyl acetoxyethanephosphonate employed, was 80% by weight.

(3) The experimental set-up was as in Example 1. After 50 g of crude vinylphosphonic acid had been put in and heated up to 210° C., 224 g per hour of diethyl 2-acetoxyethanephosphonate were added dropwise under a pressure of 5 mbar. The reflux ratio was set to 0.5. 825 g of distillate containing 74% by weight of diethyl vinylphosphonate, 21% by weight of acetic acid, 2% by weight of diethyl acetoxyethanephosphonate and 1.7% by weight of triethylphosphate were obtained in the course of 5 hours.

The product (180 g) obtained in the cold trap contained 7% by weight of diethyl vinylphosphonate, 28% by weight of acetic acid, 55% by weight of ethyl acetate and 8% by weight of ethanol. During this time the contents of the sump had increased by 115 g.

We claim:

1. A process for the production of dialkyl esters of vinyl phosphonic acid which comprises subjecting dialkyl esters of 2-acetoxyethane phosphonic acid to cleavage by contacting with an acidic liquid catalytically acting medium at a temperature in the range from 150° to 270° C. and under a pressure such that the partial pressures of the total of the components of the reaction system is in the range from 1 to 500 mbar, and drawing off the resulting dialkyl esters of vinyl phosphonic acid and other volatile reactions products.

2. A process as claimed in claim 1, wherein the cleavage is carried out at a total pressure above 500 mbar with the proviso that the differential pressure between the total pressure and the partial pressure of the total of the components of the reaction system results from a gas inert towards the components of the reaction system under the reaction conditions.

3. A process as claimed in claim 1, wherein the total pressure is adjusted in the reaction system to a range of from 1 to 500 mbar.

4. A process as claimed in claim 1, wherein the partial pressure of the total of the components of the reaction system is in the range of from 5 to 100 mbar.

5. A process as claimed in claim 2, wherein the inert gas is nitrogen, methane, ethane, carbon dioxide or a noble gas.

6. A process as claimed in claim 1, wherein the temperature is in the range of from 180° to 250° C.

7. A process as claimed in claim 1, wherein the alkyl groups of the ester each have from 1 to 8 carbon atoms.

8. A process as claimed in claim 7, wherein the alkyl groups of the ester each have from 1 to 4 carbon atoms.

9. A process as claimed in claim 8, wherein the alkyl groups of the ester each have 1 or 2 carbon atoms.

10. A process as claimed in claim 1, wherein the catalytically acting medium is applied in an amount of at least 0.1 and at most 20 %, referred to the weight of the dialkyl ester of the acetoxyethane phosphonic acid introduced in the reaction.

11. A process as claimed in claim 10, wherein the catalytically acting medium is applied in an amount of at least 1 %.

12. A process as claimed in claim 11, wherein the catalytically acting medium is applied in an amount in the range of from 1 to 5 %.

13. A process as claimed in claim 1, wherein an acidic catalytically acting medium comprising vinylphosphonic acid is used.

14. A process as claimed in claim 13, wherein a catalytically acting medium is used which has been formed in the reaction as a higher boiling by-product and subsequently has been treated in a heated state with water.

15. A process as claimed in claim 14, wherein the said byproduct has been treated with boiling water for 5 minutes to 2 hours.

16. A process as claimed in claim 1, wherein the cleavage products formed are continuously removed from the reaction zone.

17. A process for the production of di-$C_1$-$C_4$-alkyl esters of vinyl phosphonic acid which comprises subjecting di-$C_1$-$C_4$-alkyl esters of 2-acetoxyethane phosphonic acid to cleavage by contacting with a liquid acidic catalytically acting medium at a temperature in the range from 180° to 250° C. and under a pressure such that the partial pressures of the total of the components of the reaction system is in the range from 5 to 100 mbar, and drawing off the resulting dialkyl esters of vinyl phosphonic acid and other volatile reaction products.

18. A process as claimed in claim 17, wherein the alkyl groups of the ester each have 1 or 2 carbon atoms.

19. A process as claimed in claim 17, wherein an acidic catalytically acting medium is used which has been formed in the reaction as a higher boiling by-product and subsequently been treated in the hot with water.

20. A process as claimed in claim 17, wherein the cleavage products formed are continuously removed from the reaction zone.

* * * * *